United States Patent
Wang et al.

(10) Patent No.: US 10,292,965 B2
(45) Date of Patent: May 21, 2019

(54) NINTEDANIB DIETHANESULFONATE SALT CRYSTAL AND PREPARATION METHOD AND USE THEREOF

(71) Applicant: Chia Tai Tianqing Pharmaceutical Group Co., Ltd., Lianyungang (CN)

(72) Inventors: Hubo Wang, Lianyungang (CN); Xueyan Zhu, Lianyungang (CN); Meng Guo, Lianyungang (CN); Mingtong Hu, Lianyungang (CN); Jiasong Zhang, Lianyungang (CN); Jiude Sun, Lianyungang (CN)

(73) Assignee: Chia Tai Tianqing Pharmaceutical Group Co., Ltd., Jiangsu (CN)

( * ) Notice: Subject to any disclaimer, the term of this patent is extended or adjusted under 35 U.S.C. 154(b) by 18 days.

(21) Appl. No.: 15/558,050

(22) PCT Filed: Mar. 11, 2016

(86) PCT No.: PCT/CN2016/076110
§ 371 (c)(1),
(2) Date: Sep. 13, 2017

(87) PCT Pub. No.: WO2016/146020
PCT Pub. Date: Sep. 22, 2016

(65) Prior Publication Data
US 2018/0064684 A1 Mar. 8, 2018

(30) Foreign Application Priority Data

Mar. 13, 2015 (CN) .......................... 2015 1 0112909

(51) Int. Cl.
| | |
|---|---|
| *A61K 31/404* | (2006.01) |
| *A61K 31/496* | (2006.01) |
| *C07D 209/34* | (2006.01) |
| *C30B 28/04* | (2006.01) |
| *C30B 29/46* | (2006.01) |

(52) U.S. Cl.
CPC .......... *A61K 31/404* (2013.01); *A61K 31/496* (2013.01); *C07D 209/34* (2013.01); *C30B 28/04* (2013.01); *C30B 29/46* (2013.01); *A61K 2300/00* (2013.01)

(58) Field of Classification Search
CPC .................................................. A61K 31/404
See application file for complete search history.

(56) References Cited

FOREIGN PATENT DOCUMENTS

| WO | 2012068441 A2 | 5/2012 | |
|---|---|---|---|
| WO | WO-2012068441 A2 * | 5/2012 | ........... C07D 209/34 |

OTHER PUBLICATIONS

Paleo-oncology Research Organization (PRO). "What is Neoplastic Disease?" © 2018. Available from: <https://www.cancerantiquity.org/neoplastic-disease>.*
Cancer Research UK. "Can cancer be prevented?" © 2018. Available from: <http://www.cancerresearchuk.org/about-cancer/causes-of-cancer/can-cancer-be-prevented>.*
Autoimmune Registry. "List of Autoimmune Diseases—The Autoimmune Registry." © 2018. Available from: <http://www.autoimmuneregistry.org/the-list-1/>.*
Mayo Clinic. "Crohn's Disease—Prevention." © 2018. Available from: <https://www.webmd.com/ibd-crohns-disease/crohns-disease/tc/crohns-disease-prevention >.*
"Pulmonary Fibrosis." © 2018. Available from: <https://www.healthline.com/health/pulmonary-fibrosis >.*

* cited by examiner

*Primary Examiner* — Andrew D Kosar
*Assistant Examiner* — John S Kenyon
(74) *Attorney, Agent, or Firm* — Fox Rothschild LLP

(57) ABSTRACT

The present invention relates to a nintedanib diethanesulfonate salt A-type crystal represented by formula (II), and also relates to a crystalline composition and pharmaceutical composition comprising the crystal, and preparation method and use thereof. An X-ray powder diffraction spectrum of the nintedanib diethanesulfonate salt A-type crystal of the present invention has a diffraction peak at about 14.64, 18.79, 19.31, 20.11, 21.20, 22.45 and 26.71° when represented via a 2θ value. The nintedanib diethanesulfonate salt A-type crystal of the present invention has a stable property, is non-hygroscopic and difficult to degrade, and is particularly suitable for medicine production.

(II)

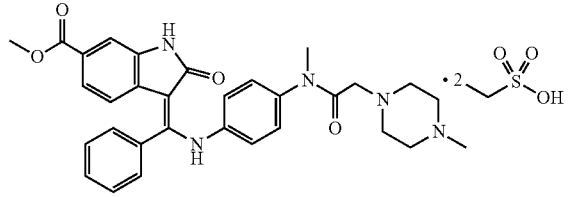

19 Claims, 1 Drawing Sheet

NINTEDANIB DIETHANESULFONATE SALT CRYSTAL AND PREPARATION METHOD AND USE THEREOF

CROSS REFERENCE TO RELATED APPLICATION

The present application claims priority to and the benefit of the Chinese patent application No. 201510112909.0 filed with the State Intellectual Property Office of China on Mar. 13, 2015, which is hereby incorporated by reference in its entirety.

TECHNICAL FIELD

The present application relates to the field of medical chemistry. More specifically, the present application relates to a nintedanib diethanesulfonate crystal, a crystalline composition, a pharmaceutical composition, and a preparation method and use thereof.

BACKGROUND

Nintedanib/intedanib, whose chemical name is 3-Z-[1-(4-(N-((4-methylpiperazin-1-yl)-methylcarbonyl)-N-methyl-amino)-anilino)-1-phenyl-methylene]-6-methoxycarbonyl-2-indolinone, has the structure represented by Formula (I):

Formula (I)

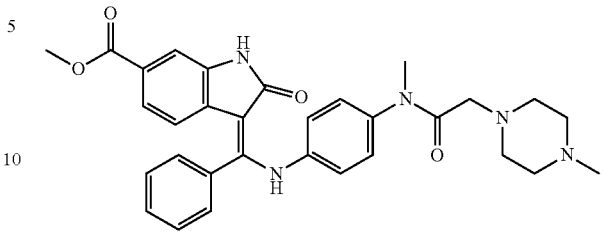

Nintedanib has inhibiting effects on various kinases, particularly receptor tyrosine kinases, such as VEGFR1, VEGFR2, VEGFR3, PDGFRα, PDGFRβ, FGFR1, FGFR3, EGFR, HER2, c-Kit, IGF1R, Flt-3 and HGFR. It can be used for the treatment of neoplastic diseases, immunological diseases or pathological conditions involving immunological components, or fibrotic diseases, especially idiopathic pulmonary fibrosis.

WO2012068441 discloses an amorphous form and a crystalline form of nintedanib diethanesulfonate of Formula (II).

Formula (II)

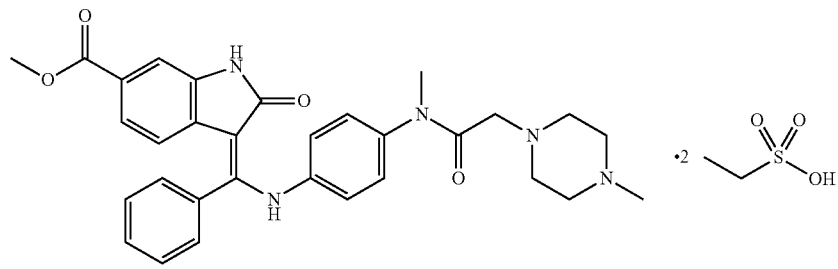

However, the above-mentioned crystalline form of nintedanib diethanesulfonate is not stable and easy to absorb moisture during storage and the content of impurities increases significantly during storage. The chemical stability, solid-state stability and shelf life of an active ingredient are very important factors from the viewpoint of obtaining a commercially viable production method or from the viewpoint of producing a pharmaceutical composition comprising an active compound. Therefore, it is very important for the production and storage of a drug to provide a suitable form of the drug having desired properties.

CONTENTS OF THE INVENTION

In one aspect, the present application provides a crystalline Form A of nintedanib diethanesulfonate represented by Formula (II), Formula (II)

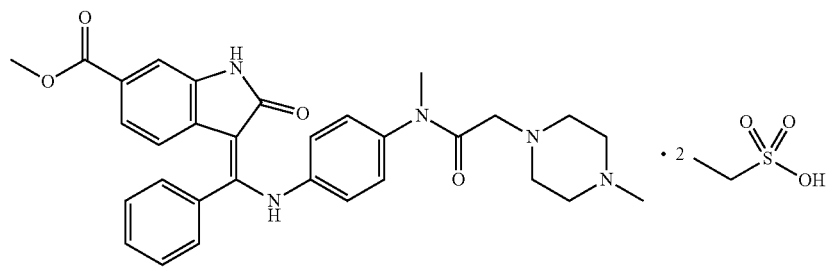

characterized in that the X-ray powder diffraction spectrum of the crystalline Form A has diffraction peaks expressed by 2θ values at about 14.64, 18.79, 19.31, 20.11, 21.20, 22.45, and 26.71 degrees (°).

In another aspect, the present application provides a crystalline composition, wherein the above-mentioned crystalline Form A of nintedanib diethanesulfonate accounts for 50% or more, preferably 80% or more, more preferably 90% or more, and most preferably 95% or more by weight of the crystalline composition.

In another aspect, the present application provides a pharmaceutical composition comprising a therapeutically effective amount of the crystalline Form A of nintedanib diethanesulfonate, or the crystalline composition described above.

In another aspect, the present application provides use of the crystalline Form A of nintedanib diethanesulfonate, the crystalline composition or the pharmaceutical composition described above in the manufacture of a medicament for the prophylaxis or treatment of a disease or disorder selected from the group consisting of neoplastic diseases, immunological diseases, pathological conditions involving immunological components, and fibrotic diseases, in particular in the manufacture of a medicament for the treatment of non-small cell lung cancer or idiopathic pulmonary fibrosis.

In another aspect, the present application provides a method for the prophylaxis or treatment of a disease or disorder selected from the group consisting of neoplastic diseases, immunological diseases, pathological conditions involving immunological components, and fibrotic diseases, comprising administering to a mammal in need thereof a therapeutically effective amount of the crystalline Form A of nintedanib diethanesulfonate, the crystalline composition or the pharmaceutical composition described above.

In another aspect, the present application provides the crystalline Form A of nintedanib diethanesulfonate, the crystalline composition or the pharmaceutical composition described above for use in the prophylaxis or treatment of a disease or disorder selected from the group consisting of neoplastic diseases, immunological diseases, pathological conditions involving immunological components, and fibrotic diseases.

In another aspect, the present application provides a method for preparing the crystalline Form A of nintedanib diethanesulfonate, or the crystalline composition described above, comprising:

(a) dissolving nintedanib and ethanesulfonic acid in an organic solvent, or dissolving nintedanib diethanesulfonate in an organic solvent; and (b) heating the resulting mixture to 40-60° C., and then adding acetone to precipitate crystals.

DETAILED DESCRIPTION

Definitions

Figure 1:
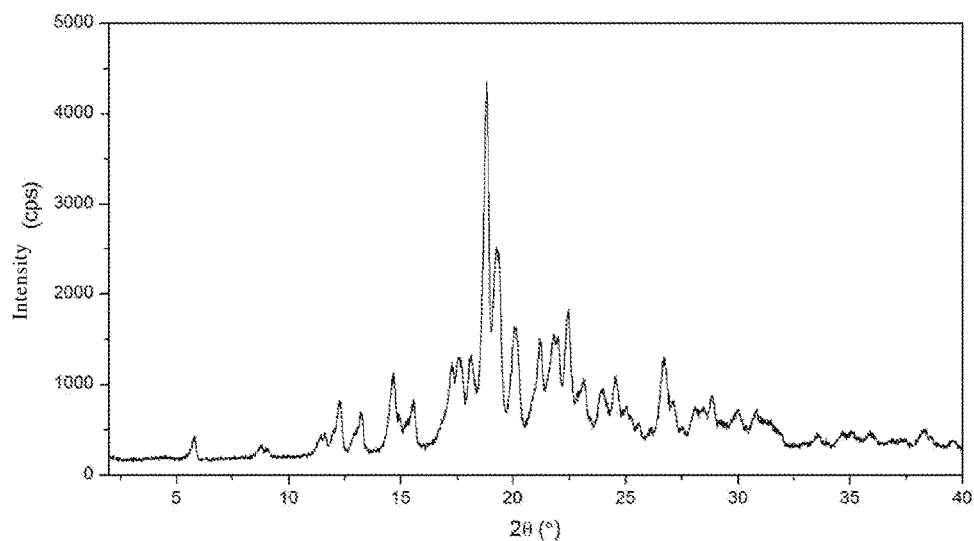
FIG. 1 is an X-ray powder diffraction pattern of the crystalline Form A of nintedanib diethanesulfonate prepared in Example 1.

Unless specifically defined otherwise, the following terms used in the specification and claims appended hereto of the present application have the following meanings.

"Mammals" include humans, domestic animals such as laboratory mammals and house pets (for example cats, dogs, pigs, cattle, sheep, goats, horses and rabbits), and non-domesticated mammals such as wild mammals and the like.

The term "pharmaceutical composition" refers to a formulation comprising the compound of the present invention and medium usually acceptable in the art for delivering a biologically active compound to a mammal (such as human) The medium includes all pharmaceutically acceptable carriers for its use. A pharmaceutical composition facilitates the administration of a compound to an organism.

The term "carrier" is defined as a compound beneficial to deliver a compound into cells or tissues. For example, dimethylsulfoxide (DMSO) is usually used as a carrier, as it can easily deliver some organic compounds into cells or tissues of an organism.

"Pharmaceutically acceptable carrier" includes but not limited to any adjuvants, excipients, glidants, sweeteners, diluents, preservatives, dyes/colorants, flavoring agents, surfactants, wetting agents, dispersing agents, suspending agents, stabilizing agents, isotonic agents, solvents or emulsifiers, which are approved by the State Drug Administration for use in humans or domestic animals.

"Therapeutically effective amount" refers to an amount of a compound of the present invention that, when administered to a mammal, preferably human, is sufficient to achieve the treatment of a viral infection in a mammal, preferably in a human, as defined hereinafter. A "therapeutically effective amount" of a compound of the present invention will vary depending on the compound, the disease condition and its severity, the route of administration and the age of the mammal to be treated. However, it can be routinely determined by those ordinary skilled in the art according to their knowledge and the disclosure of the present invention.

"Treatment" used herein includes any therapeutic treatment of a viral infection in a mammal, preferably in human, which comprises:

(i) inhibiting a viral infection, i.e., preventing its development;

(ii) ameliorating a viral infection, i.e., leading to recovering from a viral infection; or (iii) relieving symptoms caused by a viral infection.

Embodiments

In one aspect, the present application provides a crystalline Form A of nintedanib diethanesulfonate represented by Formula (II),

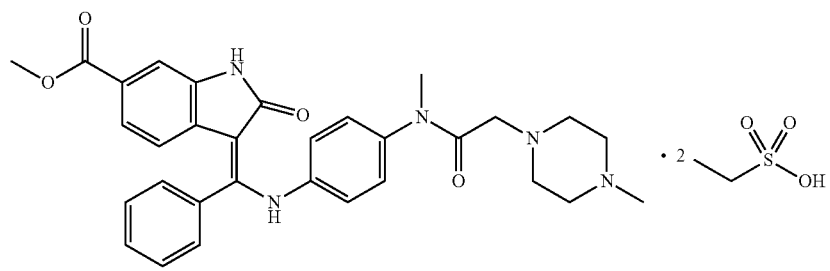

Formula (II)

characterized in that the X-ray powder diffraction spectrum of the crystalline Form A has diffraction peaks expressed by 2θ values at about 14.64, 18.79, 19.31, 20.11, 21.20, 22.45 and 26.71 degrees; typically has diffraction peaks expressed by 2θ values at 5.84, 12.27, 14.64, 17.27, 17.61, 18.12, 18.79, 19.31, 20.11, 21.20, 22.45, 24.57 and 26.71 degrees; and more typically has diffraction peaks expressed by 2θ values at 5.84, 12.27, 13.22, 14.64, 15.54, 17.27, 17.61, 18.12, 18.79, 19.31, 20.11, 21.20, 21.88, 22.45, 23.13, 23.95, 24.57 and 26.71 degrees.

In one embodiment of the present application, the X-ray powder diffraction spectrum of the crystalline Form A of nintedanib diethanesulfonate of the present application has diffraction peaks as shown in the following table.

| No. | 2θ(°) | $I/I_0$ |
| --- | --- | --- |
| 1 | 5.84 | 10 |
| 2 | 12.27 | 20 |
| 3 | 13.22 | 17 |
| 4 | 14.64 | 27 |
| 5 | 15.54 | 20 |
| 6 | 17.27 | 31 |
| 7 | 17.61 | 30 |
| 8 | 18.12 | 31 |
| 9 | 18.79 | 100 |
| 10 | 19.31 | 61 |
| 11 | 20.11 | 39 |
| 12 | 21.20 | 36 |
| 13 | 21.88 | 36 |
| 14 | 22.45 | 42 |
| 15 | 23.13 | 26 |
| 16 | 23.95 | 23 |
| 17 | 24.57 | 26 |
| 18 | 26.71 | 32 |

In one embodiment of the present application, the crystalline Form A of the nintedanib diethanesulfonate of the present application has an X-ray powder diffraction spectrum as shown in FIG. 1.

In one embodiment of the present application, the crystalline Form A of nintedanib diethanesulfonate of the present application has a differential scanning calorimetry (DSC) thermogram with an absorption peak at about 257° C.

Figure 2:
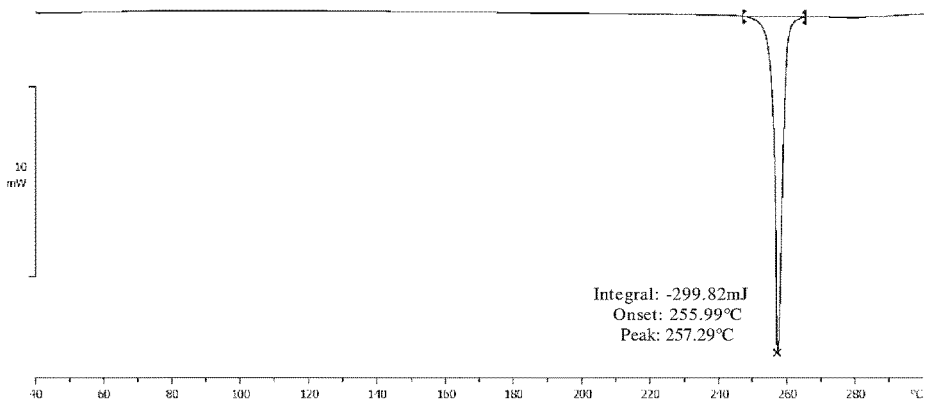
FIG. 2 is a differential scanning calorimetry (DSC) thermogram of the crystalline Form A of nintedanib diethanesulfonate prepared in Example 1.

In one embodiment of the present application, the crystalline Form A of nintedanib diethanesulfonate of the present application has a differential scanning calorimetry (DSC) thermogram as shown in FIG. 2.

In another aspect, the present application provides a crystalline composition, wherein the above-mentioned crystalline Form A of nintedanib diethanesulfonate accounts for 50% or more, preferably 80% or more, more preferably 90% or more, and most preferably 95% or more by weight of the crystalline composition.

In another aspect, the present application provides a pharmaceutical composition comprising a therapeutically effective amount of the crystalline Form A of nintedanib diethanesulfonate, or the crystalline composition described above. The pharmaceutical composition may comprise at least one pharmaceutically acceptable carrier.

In another aspect, the present application provides use of the crystalline Form A of nintedanib diethanesulfonate, the crystalline composition or the pharmaceutical composition described above in the manufacture of a medicament for the prophylaxis or treatment of a disease or disorder selected from the group consisting of neoplastic diseases, immunological diseases, pathological conditions involving immunological components, and fibrotic diseases, in particular in the manufacture of a medicament for the treatment of non-small cell lung cancer or idiopathic pulmonary fibrosis.

In another aspect, the present application provides a method for the prophylaxis or treatment of a disease or disorder selected from the group consisting of neoplastic diseases, immunological diseases, pathological conditions involving immunological components, and fibrotic diseases, comprising administering to a mammal in need thereof a therapeutically effective amount of the crystalline Form A of nintedanib diethanesulfonate, the crystalline composition or the pharmaceutical composition described above. The mammal is preferably a human.

In another aspect, the present application provides the crystalline Form A of nintedanib diethanesulfonate, the crystalline composition or the pharmaceutical composition described above for use in the prophylaxis or treatment of a disease or disorder selected from the group consisting of neoplastic diseases, immunological diseases, pathological conditions involving immunological components, and fibrotic diseases.

In another aspect, the present application provides a method for preparing the crystalline Form A of nintedanib diethanesulfonate, or the crystalline composition described above, comprising:

(a) dissolving nintedanib and ethanesulfonic acid in an organic solvent, or dissolving nintedanib diethanesulfonate in an organic solvent; and (b) heating the resulting mixture to 40-60° C., and then adding acetone to precipitate crystals.

In some embodiments, the organic solvent in the step (a) is a $C_1$-$C_6$ alkyl alcohol, preferably methanol or ethanol, and more preferably methanol. The amount of the organic solvent is able to dissolve nintedanib and ethanesulfonic acid or nintedanib diethanesulfonate. In some embodiments, 10-40 ml of the organic solvent, preferably 10-15 ml of the organic solvent is added per mole of nintedanib or nintedanib diethanesulfonate.

In some embodiments, the molar ratio of ethanesulfonic acid to nintedanib in the step (a) is 2-5:1, preferably 3:1.

In some embodiments, the nintedanib diethanesulfonate in the step (a) is an amorphous nintedanib diethanesulfonate or other crystalline forms of nintedanib diethanesulfonate, for example, the nintedanib diethanesulfonate crystal prepared according to WO2012068441.

In some embodiments, the volume of acetone in the step (b) is 2 times or more, preferably 2 to 8 times the volume of the organic solvent in the step (a). Preferably, the resulting mixture is heated to 50° C.

In some embodiments, in the step (b), acetone is added to precipitate crystals under stirring at a kept temperature (40-60° C.). That is, during the addition of acetone for crystallization, the temperature is maintained at 40-60° C.

In some embodiments, the method for preparing the crystalline Form A of nintedanib diethanesulfonate, or the crystalline composition described above further comprises:
(c) filtering; and
(d) drying.

In the present application, the X-ray powder diffraction spectrum of a sample is measured under the following conditions:
Instrument: Bruker D2 X-ray diffractometer; Test Conditions: 30 kv 10 mA; Slit: 0.6 mm/3 mm/0.8 mm; Target Type: Cu; Angle Range: 5-40°; Step Size: 0.1 s/0.02°.

In the present application, the DSC spectrum is measured under the following conditions:
Instrument: Mettler type 1 differential thermal analyzer; Temperature Range: 30-270° C.; Heating Rate: 10° C./min.

It should be noted that, in an X-ray powder diffraction (XRD) spectrum, a diffraction pattern of a crystalline compound is usually characteristic for a specific crystalline form. Relative intensities of the bands (especially at the low angles) can vary depending upon preferential orientation effects resulting from the differences of crystallization conditions, particle sizes, and other measuring conditions. Therefore, the relative intensities of diffraction peaks are not characteristic for a specific crystalline form. It is the relative positions of peaks rather than relative intensities thereof that should be paid more attention when judging whether a crystalline form is the same as a known crystalline form. In additional, as for any given crystalline form, there may be a slight error in the position of peaks, which is also well known in the field of crystallography. For example, the position of a peak may shift due to the change of a temperature, the movement of a sample or the calibration of an instrument and so on when analyzing the sample, and the measurement error of 2θ value is sometimes about ±0.2°. Accordingly, this error should be taken into consideration when identifying a crystal structure. Usually, the position of a peak is expressed in terms of 2θ angle or lattice spacing d in an XRD pattern and the simple conversion relationship therebetween is d=λ/2 sin θ, wherein d represents the lattice spacing, λ represents the wavelength of incident X-ray, and θ represents the diffraction angle. For the same crystalline form of the same compound, the position of peaks in an XRD spectrum thereof has similarity on the whole, and the error of relative intensities may be larger. In addition, it is necessary to point out that due to some factors such as reduced contents, parts of diffraction lines may be absent in the identification of a mixture. At this time, even a band may be characteristic for the given crystalline form without depending upon all the bands of a high purity sample.

DSC is used to measure a thermal transition temperature when absorbing or releasing heat due to the change of a crystal structure or the melting of a crystal. In a continuous analysis of the same crystalline form of the same compound, the error of a thermal transition temperature and a melting point is typically within a range of about ±5° C., generally within a range of about ±3° C. A compound with a given DSC peak or melting point means that the DSC peak or melting point may be varied within a range of ±5° C. DSC provides an auxiliary method to distinguish different crystalline forms. Different crystalline forms can be identified by their characteristically different transition temperatures. It is necessary to point out that the DSC peak or melting point of a mixture may vary over a wider range. Furthermore, because of the decomposition in the melting process of a substance, the melting temperature is related to a heating rate.

In the present application, nintedanib can be prepared with reference to the method disclosed in CN1671660A.

The moisture content of the crystalline Form A of nintedanib diethanesulfonate of the present application is essentially unchanged after the crystalline Form A is placed under high humidity (25° C., 92.5% RH) and accelerated test conditions (40±2° C., 75%±5% RH) for 10 days, whereas the moisture content of the crystalline form of nintedanib diethanesulfonate prepared according to WO2012068441 increases significantly under the same conditions, and it is obvious from its character that the crystalline form absorbs moisture to become clumping.

The present application will be described in further detail with reference to the following examples, but the present application is not limited to the following examples.

Example 1: Preparation of the Crystalline Form A of Nintedanib Diethanesulfonate To 11 mL of methanol was added 5.4 g of nintedanib, and about 3.3 g of ethanesulfonic acid was then added under stirring. After nintedanib and ethanesulfonic acid were dissolved to obtained a clear solution, the temperature of the resulting mixture was raised to 50° C., and then 45 mL of acetone was slowly added to precipitate crystals under stirring at the kept temperature. The crystalline Form A of nintedanib diethanesulfonate was obtained by filtration.

The resulting crystalline Form A of nintedanib diethanesulfonate has an XRD pattern as shown in FIG. 1 and a DSC thermogram as shown in FIG. 2.

Example 2: Preparation of the Crystalline Form A of Nintedanib Diethanesulfonate 7.6 g of the nintedanib diethanesulfonate crystal prepared according to WO2012068441 was added to 15 mL of methanol and dissolved by heating. Then 40 mL of acetone was slowly added to precipitate crystals under stirring at a kept temperature of 50° C. The crystalline Form A of nintedanib diethanesulfonate was obtained by filtration.

Example 3: Stability Test

According to the test method of the influence factors for active pharmaceutical ingredients described in the Chinese Pharmacopoeia, 2010 edition, Part II, Appendix XIX C, the crystalline Form A of nintedanib diethanesulfonate prepared in Example 1 and the crystalline form of nintedanib diethanesulfonate prepared according to WO2012068441 (the existing crystal) were subjected to a high-humidity test (25° C., 92.5% RH), light irradiation test (10000 lx±500 lx) and accelerated test (40° C.±2° C., a relative humidity of 75%±5%), respectively. The tests last for 10 days. Samples were taken on days 0, 5 and 10 to measure the purities of the samples so as to determine their stabilities. The test results were shown in Table 1.

TABLE 1

Stability Test Results

| Test conditions and test times | | The crystalline Form A (%) | The existing crystal (%) |
|---|---|---|---|
| initial value | day 0 | 99.80 | 99.78 |
| high-humidity | day 5 | 99.78 | 99.72 |
| | day 10 | 99.79 | 99.67 |
| light | day 5 | 99.79 | 99.73 |
| irradiation | day 10 | 99.70 | 99.19 |
| accelerated test | day 10 | 99.77 | 95.10 |

Example 4: Dissolution Rate of the Crystalline Form A of Nintedanib Diethanesulfonate Intrinsic dissolution rates of the crystalline Form A of nintedanib diethanesulfonate prepared in Example 1 and the crystalline form of nintedanib diethanesulfonate prepared according to WO2012068441 (the existing crystal) were determined by using the intrinsic dissolution rotating disk method in Chapter 1087 of the U.S. Pharmacopeia, and the results are shown in Table 2. Dissolution Medium: 700 ml of 0.1 mol/L hydrochloric acid solution, Rotating Speed: 300 rpm, Detection Wavelength: 287 nm, Medium Temperature: 37° C.

| Samples | Maximum dissolution rate (μg/ml/min) | Average dissolution rate (μg/ml/min) |
|---|---|---|
| the existing crystal | 14.689 | 13.373 |
| the crystalline Form A | 23.344 | 22.508 |

All patents, patent application publications, patent applications and non-patent publications cited in the specification of the present application are incorporated herein in their entireties by reference.

Although the present invention has been described with respect to the specific embodiments for illustration purpose, it should be understood by those skilled in the art according to the above content that various modifications may be made without departing from the spirit and scope of the invention. Accordingly, the scope of the present invention should only be defined by the claims appended hereto.

What is claimed is:

1. A crystalline Form A of nintedanib diethanesulfonate represented by Formula (II),

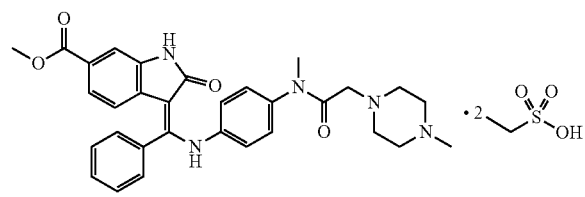

Formula (II)

wherein the X-ray powder diffraction spectrum of the crystalline Form A has diffraction peaks expressed by 2θ values at about 14.64, 18.79, 19.31, 20.11, 21.20, 22.45 and 26.71 degrees.

2. The crystalline Form A of nintedanib diethanesulfonate according to claim 1, wherein the X-ray powder diffraction spectrum of the crystalline Form A has diffraction peaks expressed by 2θ values at about 5.84, 12.27, 14.64, 17.27, 17.61, 18.12, 18.79, 19.31, 20.11, 21.20, 22.45, 24.57 and 26.71 degrees.

3. The crystalline Form A of nintedanib diethanesulfonate according to claim 2, wherein the X-ray powder diffraction spectrum of the crystalline Form A has diffraction peaks expressed by 2θ values at about 5.84, 12.27, 13.22, 14.64, 15.54, 17.27, 17.61, 18.12, 18.79, 19.31, 20.11, 21.20, 21.88, 22.45, 23.13, 23.95, 24.57 and 26.71 degrees.

4. The crystalline Form A of nintedanib diethanesulfonate according to claim 1, wherein the DSC thermogram of the crystalline Form A has an absorption peak at about 257° C.

5. A crystalline composition, wherein the crystalline Form A of nintedanib diethanesulfonate according to claim 1 accounts for 50% or more by weight of the crystalline composition.

6. A pharmaceutical composition comprising the crystalline Form A of nintedanib diethanesulfonate according to claim 1, or the crystalline composition according to claim 5.

7. A method for ameliorating or relieving the symptoms of a disease or disorder selected from the group consisting of neoplastic diseases, immunological diseases, pathological conditions involving immunological components, and fibrotic diseases, comprising administering to a mammal in need thereof a therapeutically effective amount of the crystalline Form A of nintedanib diethanesulfonate according to claim 1, the crystalline composition according to claim 5 or the pharmaceutical composition according to claim 6.

8. A method for preparing the crystalline Form A of nintedanib diethanesulfonate according to claim 1, comprising:
(a) dissolving nintedanib and ethanesulfonic acid in an organic solvent, or dissolving nintedanib diethanesulfonate in an organic solvent; and
(b) heating the resulting mixture to 40-60° C., and then adding acetone to precipitate crystals.

9. The method according to claim 8, wherein the organic solvent in the step (a) is a $C_1$-$C_6$ alkyl alcohol.

10. The method according to claim 8, wherein 10-40 ml of the organic solvent is added per mole of the nintedanib or the nintedanib diethanesulfonate in the step (a).

11. The method according to claim 8, wherein the molar ratio of the ethanesulfonic acid to the nintedanib in the step (a) is 2-5:1.

12. The method according to claim 8, wherein the volume of the acetone in the step (b) is 2 times or more the volume of the organic solvent in the step (a).

13. The method according to claim 8, wherein during the addition of acetone for crystallization in the step (b), the temperature is maintained at 40-60° C.

14. The method according to claim 8, further comprising:
(c) filtering; and
(d) drying.

15. The method according to claim 8, wherein the organic solvent in the step (a) is methanol or ethanol.

16. The method according to claim 8, wherein the organic solvent in the step (a) is methanol.

17. The method according to claim 8, wherein 10-15 ml of the organic solvent is added per mole of the nintedanib or the nintedanib diethanesulfonate in the step (a).

18. The method according to claim 8, wherein the molar ratio of the ethanesulfonic acid to the nintedanib in the step (a) is 3:1.

19. The method according to claim 8, wherein the volume of the acetone in the step (b) is 2 to 8 times the volume of the organic solvent in the step (a).

* * * * *